(12) United States Patent
Gmuer et al.

(10) Patent No.: US 8,388,587 B1
(45) Date of Patent: Mar. 5, 2013

(54) DISPOSABLE URINE COLLECTION DEVICE

(76) Inventors: Robert Gerard Gmuer, Studio City, CA (US); Toni Gmuer, Studio City, CA (US); Amy Koval, Calabasas, CA (US)

(*) Notice: Subject to any disclaimer, the term of this patent is extended or adjusted under 35 U.S.C. 154(b) by 136 days.

(21) Appl. No.: 13/019,920

(22) Filed: Feb. 2, 2011

Related U.S. Application Data

(60) Provisional application No. 61/302,883, filed on Feb. 9, 2010.

(51) Int. Cl.
*A61F 5/44* (2006.01)
*A61F 13/15* (2006.01)

(52) U.S. Cl. .......... 604/347; 604/354; 604/385.19; 604/385.201; 604/385.23; 604/392; 604/398

(58) Field of Classification Search .......... None
See application file for complete search history.

(56) References Cited

U.S. PATENT DOCUMENTS

| | | | | |
|---|---|---|---|---|
| 6,468,256 | B1 * | 10/2002 | Mishima | 604/385.14 |
| 6,668,388 | B2 * | 12/2003 | Buttigieg | 4/144.2 |
| 2002/0193762 | A1 * | 12/2002 | Suydam | 604/327 |
| 2005/0182379 | A1 * | 8/2005 | Olsen et al. | 604/385.13 |
| 2007/0270716 | A1 * | 11/2007 | Wu et al. | 600/580 |

* cited by examiner

*Primary Examiner* — Melanie Hand
*Assistant Examiner* — Joshua Lee
(74) *Attorney, Agent, or Firm* — Kelly & Kelley, LLP

(57) ABSTRACT

A disposable urine collection pouch made from diaper-like material formed in the shape of an elongated tube having an open top end and a closed bottom end. The open top end includes a funnel that leads from the opening down into the elongated tube. The elongated tube includes a superabsorbent layer to lock in and retain moisture introduced into the pouch. The funnel is made from a resilient material that flexes between a default closed position and an open position upon the exertion of sufficient and appropriate pressure by a user. After use, the pouch may be folded and disposed of in a plastic bag or otherwise deposited in a trash receptacle.

14 Claims, 5 Drawing Sheets

DISPOSABLE URINE COLLECTION DEVICE

BACKGROUND OF THE INVENTION

The present invention is directed to a disposable urine collection device. More particularly, the present invention is directed to such a device that can be used when one is travelling or otherwise outside of their home and does not want to use a public restroom.

Currently, there are a number of alternate devices and methods for urine collection, as follows:

- A urine collection bottle as used in a medical office. The drawbacks of this product are that once urinated into one has to carry around the bottle until one finds a place to dispose of the urine. Then one has to carry around the bottle until it can be washed and sanitized for future use. The urine collection bottle is not very conducive for female use as it would be extremely easy for a female to miss the opening of the bottle when urinating.
- A female urination cone made for women to use while standing over a toilet. The drawbacks of this product are that one needs to be over a toilet in order to use this product otherwise the urine just shoots out the end of the urination cone.
- One can urinate into a cup which must be carried around until a disposal location is found as with the bottle discussed above. One must also be extra careful not to spill the urine until a disposal place is found.
- A sealable bag, i.e., Ziploc bag. One then has a bag of urine which can leak or pop open before a disposal location is found.
- Bushes, trees or other foliage. Such locations are more often than not illegal but can be dirty, non-private, filled with insects, and will most likely turn muddy once urinated in.
- Public restrooms. Not only are many public restrooms extremely unsanitary, but they can simply be dirty or not well maintained. Often there are fresh urine drops on the seat that are visible to the human eye. There are always germs from urine and feces on the toilet seat and floor that are unseen.

There exists a genuine concern on the part of parents with small children for there to be sanitary facilities for their children's urination requirements when away from home. Given the unsanitary conditions of most public restrooms, a creditable survey shows that 39% of those surveyed worry about getting germs from public restrooms more than from any other source. The unsanitary conditions posed by public restrooms include germ laden toilet seats that have been exposed to and contacted by feces and urine (along with those slipping toilet seat covers and a child's propensity to touch everything, and want to grab onto the toilet seat to stop from falling in).

There is also the presence of airborne particles that carry germs. Salmonella and shigella bacteria are most likely in public restrooms, as well as, flu, *meningitis, streptococcus, staphylococcus, E. coli*, common cold and hepatitis viruses are all found in public restrooms. Then there are public door handles, faucets, sinks, walls, and public restroom floors that are germ laden from exposure to urine, feces, and airborne particles carrying germs. It is now recommended that you face away from a flushing toilet and exit quickly as airborne particles could cause germs to reach your respiratory passageways.

All of this coupled with the world's fear of a pandemic has brought about a very real and ever increasing public awareness of the dangers of unsanitary conditions and the absolute necessity to exercise all available precautions. All of this leaves parents and guardians reluctant and uneasy about the use of public restrooms for their small children. Additionally we have the overwhelmingly embarrassing necessity of men having to bring small girls into the men's public restroom, which often times have open urinals for all to see. Or the same with mothers feeling uncomfortable bringing boys into a women's restroom. Men or women when out without a member of the opposite sex can have an almost insurmountable problem with a five year old of the opposite sex.

The disposable urine collection pouch eliminates such concerns associated with a child's urination in a public restroom. It provides a simple and sanitary process to eliminate urine without the necessity of having to use an unsanitary public bathroom, thus bringing peace of mind and security to parents and guardians alike. Whether traveling on the road in a car or used as a sanitary convenience at a park, the beach, camping, at the mall, etc. it provides a real and necessary solution to problems faced today by society and can be used by all age groups. Anyone from a potty trained child to those adults and seniors concerned for their health and convenience of use can benefit greatly from the inventive disposable urine collection pouch.

Accordingly, there is a need for a device to facilitate one's need to urinate when away from home and public facilities are not a viable option. The present invention fulfills this need and provides other related advantages.

SUMMARY OF THE INVENTION

The present invention is directed to a disposable urine collection pouch, comprising an elongated tube having an open first end and a closed second end, a funnel having a mouth of the funnel disposed in the open first end and a stem of the funnel oriented such that it extends into the elongated tube toward the closed second end, and an absorbent material disposed in the elongated tube proximate to the closed second end. The elongated tube has an outer surface comprising a generally moisture-resistant material and an inner surface comprising a distribution material. The absorbent material is disposed between the outer surface and inner surface of the elongated tube. The outer surface is made from polyethylene film, a nonwoven and film composite material, or other similar material that prevents moisture transfer. The distribution material transfers moisture from the interior of the elongated tube to the absorbent material. The absorbent material preferably comprises a superabsorbent polymer or other similar absorbent material.

The funnel comprises a moisture-resistant, resilient material and is covered in a soft, absorptive material. The mouth of the funnel has an elongated, diamond-shape that defaults to a closed position and is configured to snap into an open position when pressure is applied to ends of the long axis. The mouth of the funnel in the open position is configured to cover a user's genitals.

The pouch also includes a pocket on an outer surface of the elongated tube proximate the closed second end. The elongated tube is foldable along a transverse line about mid-way between the open first end and the closed second end. The open first end is configured so as to be insertable into the pocket when the elongated tube is folded along the transverse line. A securing strap is included adjacent to the pocket and configured for fastening to the elongated tube when it is folded along the transverse line. A sanitary wipe and a disposable trash bag are included in the pocket.

Other features and advantages of the present invention will become apparent from the following more detailed description taken in connection with the accompanying drawings, which illustrate, by way of example, the principles of the present invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
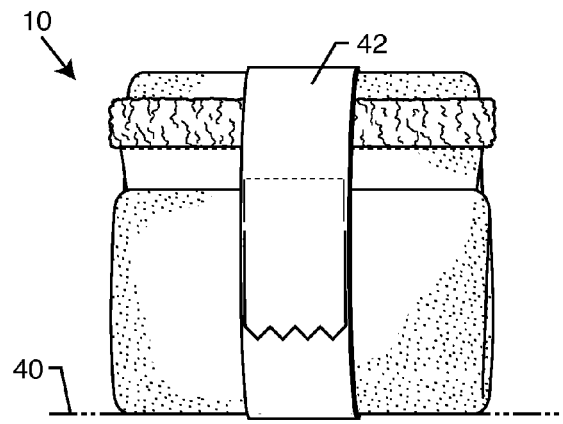
FIG. 1 is a front view of a folded disposable urine collection pouch of the present invention.
Figure 2:
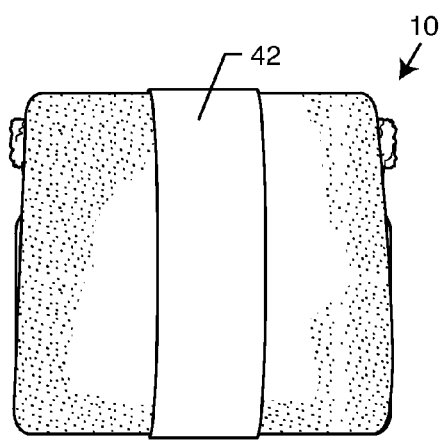
FIG. 2 is a back view of a folded disposable urine collection pouch of the present invention.
Figure 3:
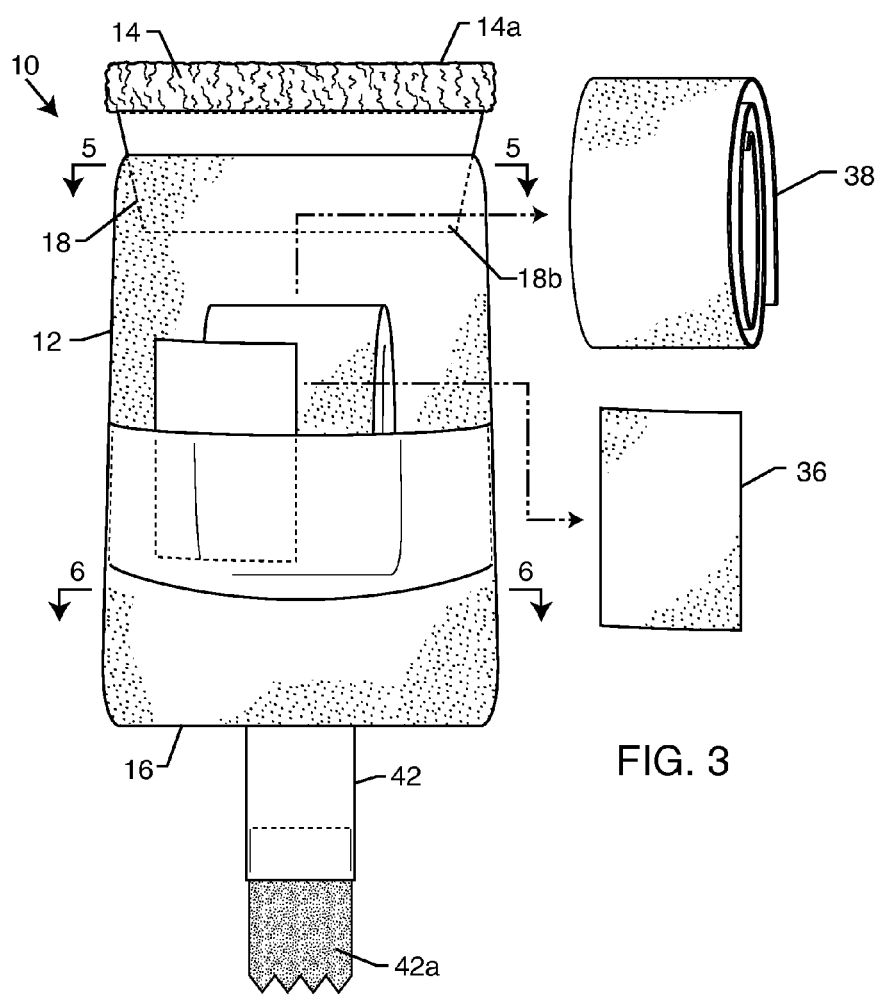
FIG. 3 is a front view of a disposable urine collection pouch of the present invention.
Figure 4:
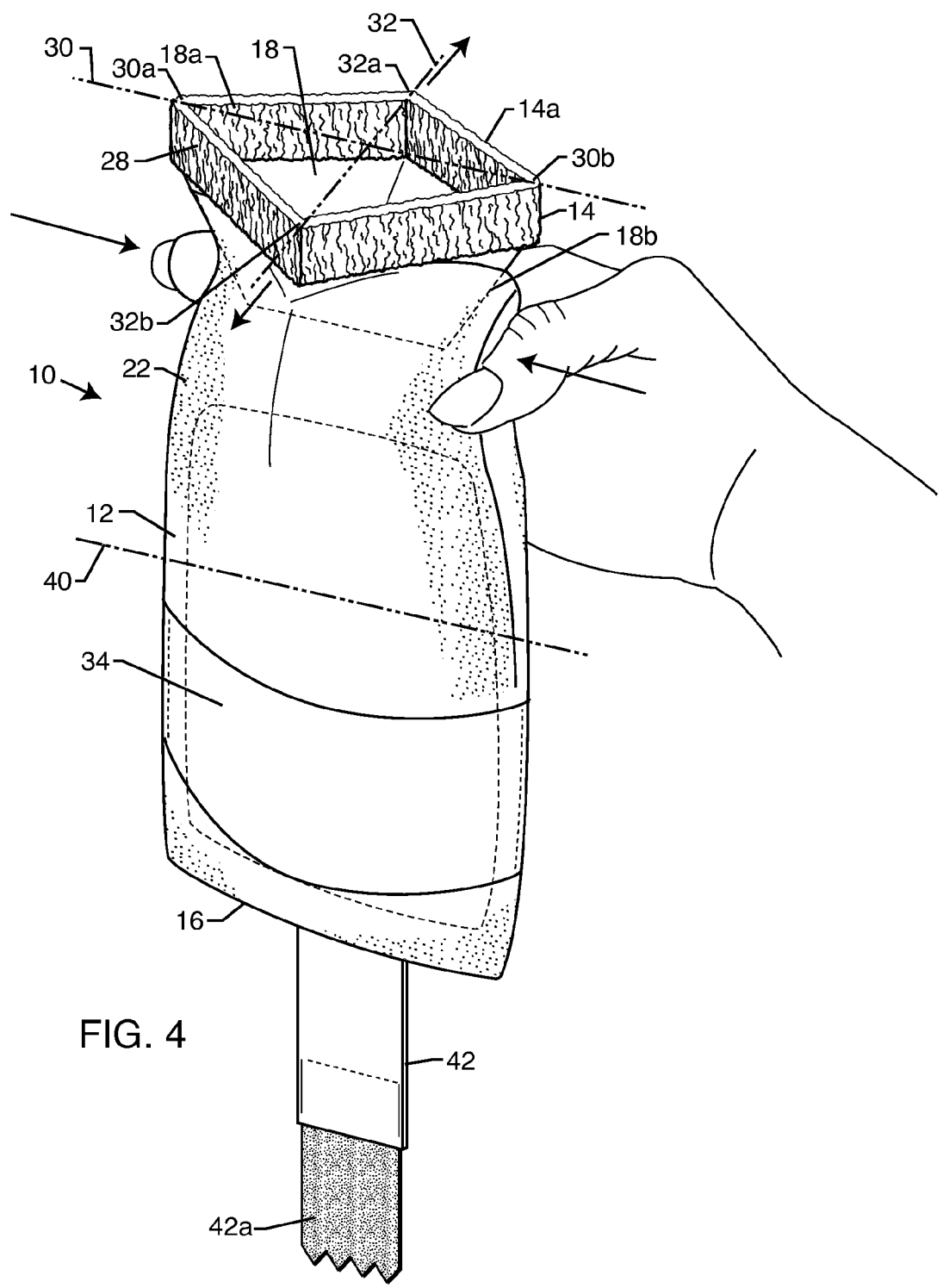
FIG. 4 is a perspective view of a disposable urine collection pouch of the present invention showing the funnel opened.
Figure 5:
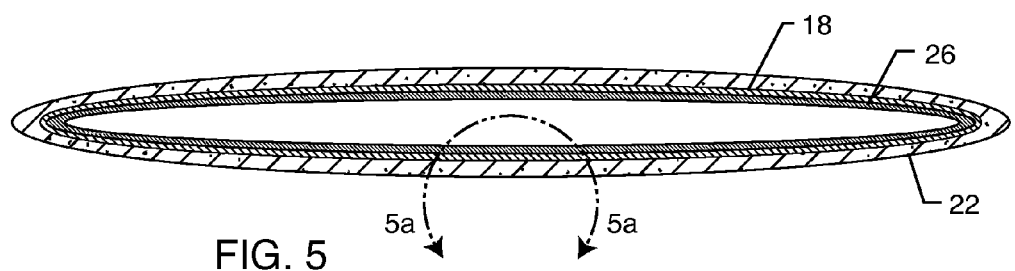
FIG. 5 is a cross-sectional view taken along line 5-5 of FIG. 3.
Figure 5A:
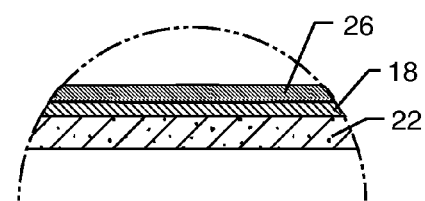
Figure 6:
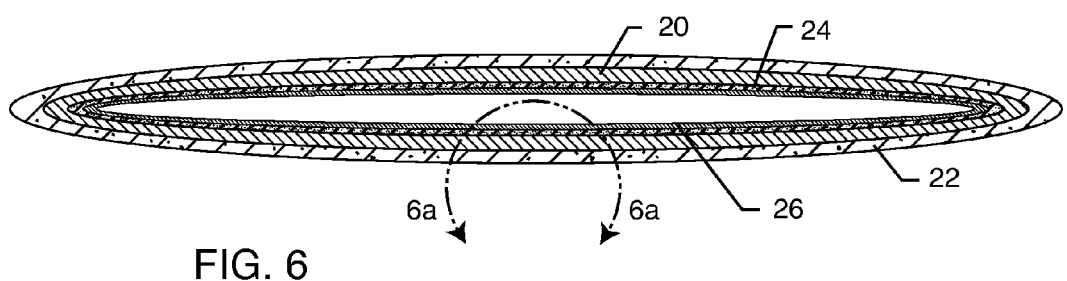
FIG. 6 is a cross-sectional view taken along line 6-6 of FIG. 3.
Figure 6A:
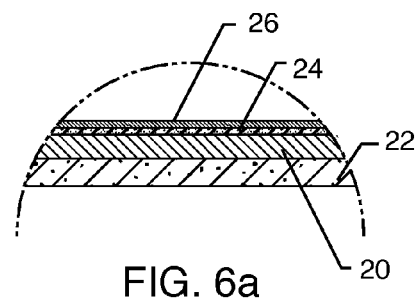

As depicted in FIGS. 1-7, the present invention is directed to a disposable urine collection pouch configured for ease of use and storage when on the go and disposal at an appropriate time. As discussed briefly above, the pouch 10 is generally made from a diaper-like material and can have an interior construction similar to any type of similarly disposable diaper. However, rather than have a diaper configured for fitting around the legs, groin and buttocks area of a person, the pouch 10 is sealed on three sides (left, right and bottom) to form the elongated tube 12 with a single opening 14 at the top to receive and collect urine or similar waste. The opening 14 is configured to be disposed proximate to the groin/genitals area of a person and collected urine. The manner of use of the pouch 10 will be described further below.

In a preferred embodiment, the urine collection pouch 10 is generally rectangular in shape and is made of fully absorbent, sanitary and disposable diaper-like material. The elongated tube 12 forms a leak proof pouch sealed and enclosed on three sides—left, right and bottom. The top of the tube 12 has an opening 14 for receiving urine or waste fluid to be collected. The edges 14a of the opening are covered in an absorbent, cushioned diaper/tissue-like material for utmost comfort when in contact with human skin, although the pouch 10 is designed so that it never need contact skin as an added sanitary measure.

As described, the pouch 10 comprises an elongated tube 12 having an open first end 14 and a closed second end 16. A funnel 18 is disposed in the open first end 14 on the interior of the elongated tube 12. The mouth 18a of the funnel 18 is positioned in the open first end 14 so that the edge of the mouth 18a is almost co-terminus with the edge 14a of the open first end 14. The stem or spout 18b of the funnel 18 is oriented such that it extends down into the elongated tube 12 toward the closed second end 16. An absorbent material 20 is disposed in the elongated tube 12 proximate to the closed second end 16. As described below, the absorbent material 20 is disposed in between outer and inner surface/layers of the tube 12.

In a preferred embodiment, the elongated tube 12 has a layered construction, which allows the transfer and distribution of urine to a core absorbent material 20 where it is locked in. As with disposable diapers, the basic layers comprise an outer surface 22 of breathable polyethylene film or a similar nonporous, nonwoven-film composite which prevents the transfer of moisture. The inner absorbent material 20 is a mixture of air-laid paper and superabsorbent polymers for wetness retention. An air-laid paper, as opposed to a wet-laid paper, is a textile-like material categorized as a nonwoven material made from fluff pulp. Compared to wet-laid paper, air-laid paper is very bulky, porous and soft with good water absorption properties. An example of a superabsorbent polymer is a poly-acrylic acid sodium salt, i.e., sodium polyacrylate, although other forms of superabsorbent polymers would work equally as well.

In a diaper, the inner layer or layer nearest the skin comprises a porous, nonwoven material with a distribution layer directly beneath which transfers wetness to the absorbent layer. In the inventive pouch 10, a distribution material 24 is included in the interior of the elongated tube 12 to effectively transfer urine waste to the absorbent material 20 and trap the same. A porous, nonwoven material is not necessary for the interior of the elongated tube 12 as is not designed to come into contact with human skin. However, such a porous, nonwoven material or interior layer 26 is preferably included to at least cover the surface of the funnel 18, as well as the edge 14a and mouth 18a. This interior layer 26 should be soft and absorbent for comfort in the event of contact with skin and to prevent spillage when collecting urine. Although not necessary for this invention, the interior layer 26 may extend down into the elongated tube 12 so as to cover the entire interior of the elongated tube 12. A layer of padding 28 may also be included around the edge of the mouth 18a for added comfort in the event of contact with the groin or genitals. The interior layer 26 may include a wetness indicator. Such wetness indicator preferably comprises a chemical in the material of the layer 26 that changes color in the presence of moisture to alert the user that the pouch 10 has been used.

Figures 7, 8:
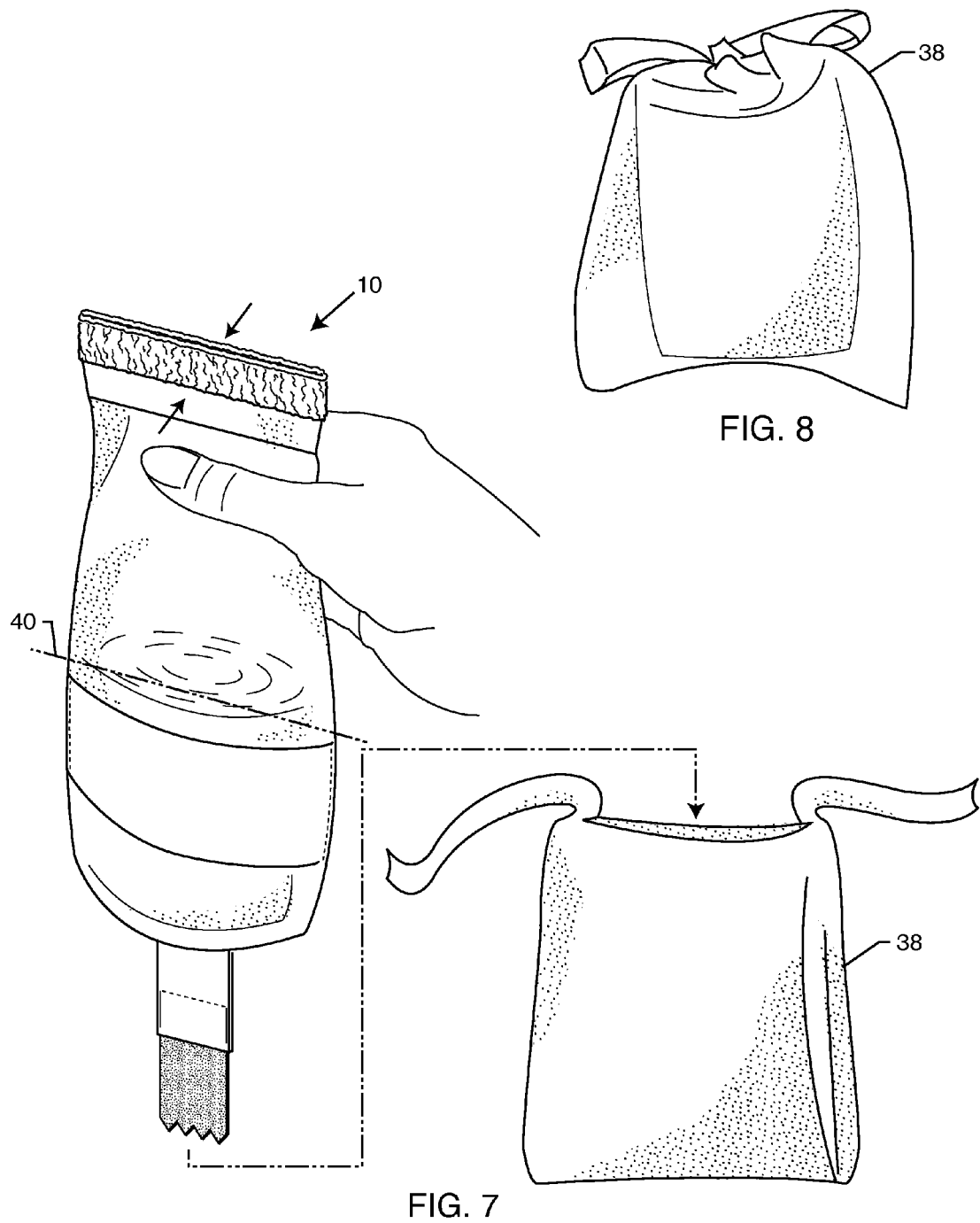
FIG. 7 is a perspective view of a disposable urine collection pouch of the present invention showing a used pouch ready to be secured by a strap and placed in a disposable bag.
FIG. 8 is a front view of a disposable urine collection pouch of the present invention showing a used pouch in a tied disposable bag.

As described, the funnel 18 is preferably a flat, interior funnel that extends down into the pouch. The funnel 18 is made of a resilient, moisture resistant material, i.e., coated poster board or other similar material. The shape of the mouth 18a on the funnel 18 approximates an elongated diamond-shape having a long axis 30 and a perpendicular short axis 32. The funnel 18 itself is resilient or flexible such that it is moveable between an open position (FIG. 4) and a closed position (FIG. 7). The default position for the mouth 18a is the closed position—meaning that the end points 32a, 32b on the short axis are nearly abutting. When a user applies pressure near the end points 30a, 30b of the long axis, i.e., within about 1½" from the edge 14a of the open first end 14, the mouth 18a moves to the open position. Once the pressure is released, the mouth 18a returns to the closed position.

The pouch 10 includes on its outer surface 22, preferably near the closed second end 16, a pocket 34 made from material similar to the material that comprises the outer surface 22 itself. The pocket 34 is intended to contain a tissue 36 for wiping and a small plastic bag 38 for disposal of a used pouch 10. The elongated tube 12 is preferably configured so as to be foldable along a transverse line 40 located about midway between the open first end 14 and the closed second end 16. This foldable feature is designed to make the pouch 10 more compact both for storage before use and for disposal after use.

In combination with the foldable feature, the pocket 34 may be configured so as to accommodate the open first end 14 when the pouch 10 is folded. In this way, the pocket 34 is configurable with elasticized fabric or material with similarly stretchable properties. By inserting the open first end 14 into the pocket 34, the pouch 10 becomes more securely closed for disposal after use. The pouch 10 may also include a securing strap 42, preferably at or near the closed second end 16. The securing strap 42 is for fastening to the pouch 10 when folded. This strap 42 includes a securing means 42a which may comprise an adhesive, a hook and loop connection (i.e., VEL-CRO®), or other similar securing methods.

The pouch 10 may also include a fragrance, lotion or essential oil in order to help mask the scent of a used pouch 10 or to protect the skin of the user.

Figure 9:
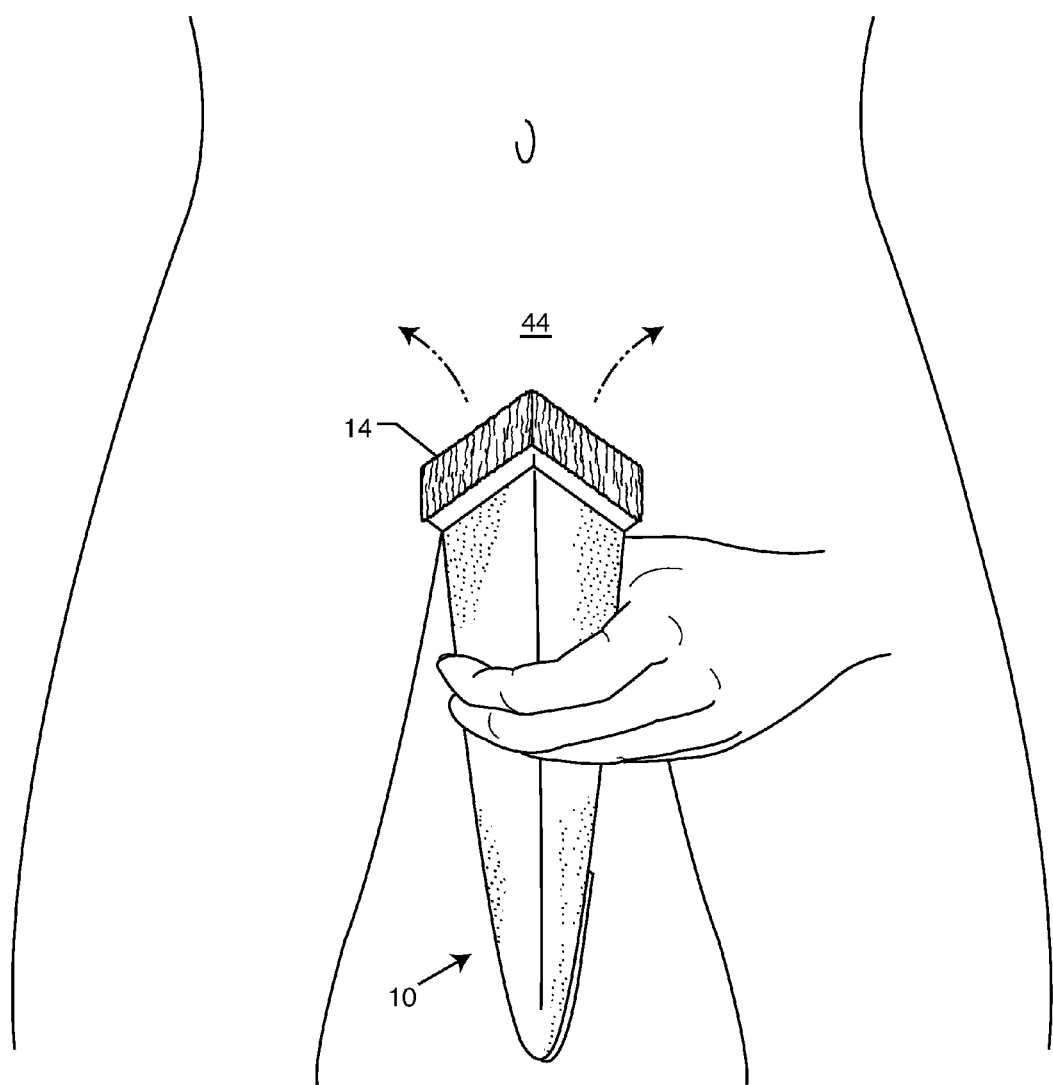
FIG. 9 is an environmental view illustrating the use of a disposable urine collection pouch of the present invention.

The disposable urine collection pouch 10 is used by opening the mouth 18a of the funnel 18 as described above. As shown in FIG. 9, one then holds the open first end 14 close to or flush up against the groin/genital area 44 of the user surrounding the genitals. The user may then urinate into the funnel 18, which acts as a fluid receiving chamber that immediately drains the urine down into the elongated tube 12 where it is distributed to the absorbent material 20. The non-porous nature of the outer layer 22 prevents any moisture from passing through the elongated tube 12. The absorbent material 20 securely locks in the urine so that it cannot leak out.

The user can then remove the tissue 36 and bag 38 from the pocket 34. The tissue is then used to wipe away any trace of urine and 36 may be placed inside of the funnel 18 or otherwise set aside for later disposal. The pouch 10 is then folded along the transverse line 40. The first end 14 may or may not be inserted inside of the pocket 34. In either case, the securing strap 42 may be used to maintain the pouch 10 in a folded position. The folded pouch 10 is then placed inside of the bag 38 and tied shut for subsequent disposal. If not placed inside of the funnel 18, the tissue 36 may also be placed inside of the bag 38 prior to tying.

Although a preferred embodiment of the invention has been described for purposes of illustration, various modifications may be made without departing from the spirit and scope of the invention.

What is claimed is:

1. A disposable urine collection pouch, comprising:
    an elongated tube having an open first end and a closed second end;
    a funnel made from a moisture-resistant, resilient material and having a mouth of the funnel disposed in the open first end and a stem of the funnel oriented such that it extends into the elongated tube toward the closed second end, wherein the mouth of the funnel has an elongated, diamond-shape that defaults to a closed position and is configured to snap into an open position when pressure is applied to ends of the long axis; and
    an absorbent material disposed in the elongated tube proximate to the closed second end.

2. The disposable urine collection pouch of claim 1, wherein the elongated tube has an outer surface comprising a moisture-resistant material and an inner surface comprising a distribution material.

3. The disposable urine collection pouch of claim 2, wherein the absorbent material is disposed between the outer surface and inner surface of the elongated tube.

4. The disposable urine collection pouch of claim 2, wherein the outer surface is made from polyethylene film or a nonwoven and film composite material that prevents moisture transfer.

5. The disposable urine collection pouch of claim 2, wherein the distribution material transfers moisture from the interior of the elongated tube to the absorbent material.

6. The disposable urine collection pouch of claim 1, wherein the absorbent material comprises a superabsorbent polymer.

7. The disposable urine collection pouch of claim 1, wherein the funnel is covered in a soft, absorptive material.

8. The disposable urine collection pouch of claim 1, wherein the mouth of the funnel in the open position in configured to cover a user's genitals.

9. The disposable urine collection pouch of claim 1, further comprising a pocket on an outer surface of the elongated tube proximate the closed second end.

10. The disposable urine collection pouch of claim 9, wherein the elongated tube is foldable along a transverse line about mid-way between the open first end and the closed second end.

11. A disposable urine collection pouch, comprising:
    an elongated tube having an open first end and a closed second end, with a pocket on an outer surface of the elongated tube proximate the closed second end, wherein the elongated tube is foldable along a transverse line about mid-way between the open first end and the closed second end, wherein the open first end is configured so as to be insertable into the pocket when the elongated tube is folded along the transverse line;
    a funnel having a mouth of the funnel disposed in the open first end and a stem of the funnel oriented such that it extends into the elongated tube toward the closed second end; and
    an absorbent material disposed in the elongated tube proximate to the closed second end.

12. A disposable urine collection pouch, comprising:
    an elongated tube having an open first end and a closed second end, with a pocket on an outer surface of the elongated tube proximate the closed second end, wherein the elongated tube is foldable along a transverse line about mid-way between the open first end and the closed second end;
    a securing strap adjacent to the pocket configured for fastening to the elongated tube when it is folded along the transverse line;
    a funnel having a mouth of the funnel disposed in the open first end and a stem of the funnel oriented such that it extends into the elongated tube toward the closed second end; and
    an absorbent material disposed in the elongated tube proximate to the closed second end.

13. The disposable urine collection pouch of claim 9, further comprising a sanitary wipe in the pocket.

14. The disposable urine collection pouch of claim 9, further comprising a disposable trash bag in the pocket.

* * * * *